United States Patent [19]
Rubin et al.

[11] Patent Number: 6,166,280
[45] Date of Patent: *Dec. 26, 2000

[54] CATALYST FOR THE DEHYDROGENATION OF ETHYLBENZENE TO STYRENE

[75] Inventors: Carlo Rubin, San Fermo Della Battaglia; Luigi Cavalli; Esterino Conca, both of Novara, all of Italy

[73] Assignee: Montecatini Technologies S.r.l., Milan, Italy

[ * ] Notice: This patent issued on a continued prosecution application filed under 37 CFR 1.53(d), and is subject to the twenty year patent term provisions of 35 U.S.C. 154(a)(2).

[21] Appl. No.: 08/814,191

[22] Filed: Mar. 10, 1997

[30] Foreign Application Priority Data

Mar. 8, 1996 [IT] Italy .................. MI96A0447

[51] Int. Cl.$^7$ ...................... C07C 2/64
[52] U.S. Cl. .......... 585/445; 585/444; 502/325; 502/338; 502/303; 502/304; 502/306; 502/316
[58] Field of Search ................... 502/303, 304, 502/306, 316, 325, 335; 585/443, 444, 445, 319, 440, 441; 568/474

[56] References Cited

U.S. PATENT DOCUMENTS

| | | | |
|---|---|---|---|
| 4,707,309 | 11/1987 | Voss et al. | 264/12 |
| 5,082,819 | 1/1992 | Boeck et al. | |
| 5,330,958 | 7/1994 | Viola et al. | 567/472 |

FOREIGN PATENT DOCUMENTS 0 591572  4/1994  European Pat. Off. .

OTHER PUBLICATIONS

Encyclopedia of Chemical Technology, Kirk–Othmer, vol. 18, pp. 304–305, 1991.
European Search Report for EP 97 10 3427. (Jun./1997).

*Primary Examiner*—Tom Dunn
*Attorney, Agent, or Firm*—Bruce Cave LLP

[57] ABSTRACT

Catalysts in the form of cylindrical hollow granules, suitable for the dehydrogenation of ethylbenzene to styrene, and comprising, as active component, ferric oxide and promoters chosen among oxides of alkaline or alkaline-earth metals, oxides of elements of the lanthanide series, and chromium, tungsten, and molybdenum oxides, characterized by the absence of macroporosities with a radius of more than 50,000 Å and/or by high mechanical characteristics of resistance to axial breaking and to abrasion.

12 Claims, No Drawings

CATALYST FOR THE DEHYDROGENATION OF ETHYLBENZENE TO STYRENE

The present invention relates to catalysts in the form of hollow granules having a specific geometric shape and suitable for the dehydrogenation of ethylbenzene to styrene.

A previous and currently pending application of the Applicant discloses catalysts having a complex geometric shape, for example a hollow cylindrical shape with a circular or multilobed transverse cross-section with through holes at the various lobes, obtained by compression-molding of powders (tableting), using a lubricant applied to the walls of the molding chamber and to the plungers of the mold for lubrication.

The resulting catalysts are characterized by constant size parameters, high abrasion- and breakage-resistance characteristics, and very narrow pore radius distribution. By virtue of the above mentioned type of porosity and of the high ratio between the geometrical area and the volume of the particles, the catalysts allow to considerably reduce the pressure drop that occur in a fix-bed reactor and to significantly improve the activity and selectivity of the catalyst.

BACKGROUND OF THE INVENTION

In patent literature concerning catalytic dehydrogenation of ethylbenzene to styrene, the interest has almost always been directed towards improving and optimizing the chemical composition in order to achieve ever more satisfactory performances. The improvements are generally obtained by varying the composition as regards the main components or by using different promoters.

Limited attention has been given so far to the geometry of the catalyst.

The importance of the shape can be directly correlated to the pressure used in the processes. Since the dehydrogenation reaction is accompanied by an increase in volume, a pressure reduction facilitates the shifting of the equilibrium towards the products (styrene and hydrogen), with a consequent improvement of the conversion. The possibility of modifying the shape of the catalyst so as to allow operation at a lower pressure (thus also reducing the pressure drop in the catalyst bed) is therefore desirable.

Furthermore, the dehydrogenation reaction is carried out in the presence of steam to reduce the partial pressure of styrene to shift the equilibrium towards the formation of styrene.

In order to solve this problem, two modifications have been adopted as regards the shape:

1) the granule diameter has been increased (to 5 mm) without altering its length. This has solved the problem only to a very limited extent, since a decrease in the pressure drop has indeed been achieved, owing to the reduced bulk density (and therefore owing to an increase in the void fraction), but at the same time the geometric surface exposed to catalysis has decreased. The result of these two contrasting effects has been a reduction in performance.
2) a three- or five-lobed geometric shape has been introduced. A slight improvement has been achieved in this case. However, one should bear in mind that the lobed shape has the drawback that powder forms more easily, since the lobes are weaker fracture points with respect to the solid cylindrical shape.

Industrially, the process used for catalyst shaping is extrusion molding. It should be noted that this technologically simple process has a very important limitation: specifically, it does not allow to obtain complex geometric shapes, particularly hollow shapes.

As regards composition, catalysts for the dehydrogenation of ethylbenzene to styrene comprise iron oxide, oxides of alkaline or alkaline-earth metals, and other oxides chosen among cerium, molybdenum, tungsten, and chromium oxide.

The life of the catalysts can be improved by adding chromium oxide as a stabilizer. U.S. Pat. No. 3,360,597 discloses catalysts which contain 0.5–5% $Cr_2O_3$ next to 80–90% $Fe_2O_3$ and 9–18% $K_2CO_3$. The catalyst is prepared according to a process which entails the mixing in water of yellow iron oxide, chromium oxide, and potassium carbonate so as to obtain a paste from which the catalyst is obtained in the form of cylindrical granules by extrusion, drying, and calcination.

U.S. Pat. No. 5,023,225 discloses a catalyst for the dehydrogenation of ethylbenzene to styrene which is based on iron oxide, oxides of alkaline or alkaline-earth metals, and cerium, molybdenum, or tungsten oxide, characterized in that the yellow iron oxide is blended with small amounts of chromium oxide prior to molding the catalyst. The molding process is characterized in that the yellow iron oxide blended with chromium oxide is heated to 500–1000° C. to be converted into red iron oxide before mixing the components in the form of a wet paste. Molding is performed by extrusion.

SUMMARY OF THE INVENTION

The dehydrogenation catalysts according to the invention have a hollow geometric shape (with one or more through holes) obtained by compression-molding (tableting) with a method in which the lubricant to be used is not dispersed in the bulk of the powder to be formed (bulk lubrication) but is applied to the walls of the molding chamber and to the plungers of the mold (external lubrication). DETAILED DESCRIPTION OF THE INVENTION The resulting catalysts have, with respect to those prepared by using bulk lubrication, a higher porosity, a narrower pore radius distribution, and reduced macroporosity. Porosity is generally between 0.15 and 0.35 $cm^3/g$ (determined by mercury absorption). The surface area is generally between 1 and 6 $m^2/g$ (determined by BET method). The pore distribution curve does not include macroporosities with an average pore radius of more than 50,000 Å. More than 50% of the porosity has an average radius of more than 600 Å. More preferably, the average radius is between 800 and 1800 Å.

The catalysts furthermore have constant size parameter values. Constancy of the size parameters instead cannot be obtained with molding processes that use internal lubrication, owing to considerable microcracks which occur on part or all of the catalyst particle, causing embrittlement and subsequent deformation thereof.

Because of these deformations, the compression-molding process which uses bulk lubrication has never been used in industrial practice for the production of hollow granular catalysts. It has furthermore been found that the catalysts according to the invention are characterized by mechanical properties, particularly by an axial ultimate tensile strength (in the direction of the axis of the holes), considerably higher than those of the corresponding catalysts obtained by bulk lubrication. The axial ultimate tensile strength is higher than 15 N/particle and is preferably between 20 and 80 N/particle. Abrasion-resistance is also high. The percentage of powder is generally less than 3%. In catalysts obtained by extrusion, abrasion-resistance is generally between 4 and 8% by weight. The catalysts according to the invention, by virtue of the fact that they are hollow, allow to achieve a higher conversion, for the same weight, with respect to solid-shaped catalysts.

Furthermore, the greater presence of voids provided by these catalysts allows to operate, for an equal fed flow-rate, at lower process pressures than required when using solid-shaped catalysts.

The greater presence of voids allows to operate with steam/ethylbenzene ratios higher than those usable with the catalysts having a solid shape, thus obtaining increased conversion for an equal process pressure.

The steam/ethylbenzene weight ratio usable with the catalysts of the invention is higher than 1.5 and can arrive to 2.5 or more.

The presence of holes allows to work with a lower wall thickness than in solid-shaped catalysts and therefore to better use the catalytic mass. The minimum wall thickness that can be achieved with these catalysts is between 0.6 and 0.8 mm.

For the same weight, the catalytic mass that can be used with the catalysts according to the invention is at least 1.5 times higher than that of solid-shaped catalysts having a minimum diameter of 3 mm which is compatible with the mechanical performances for practical use.

The pressure drop observed with the three-lobed catalysts according to the invention is at least 1.3 times lower than that of solid-shaped catalysts for an equal exposed geometric surface.

The lubricants that can be used to prepare the catalysts according to the invention include solids and liquids capable of reducing the friction coefficient between the powder to be tableted and the parts of the tableter that make contact with said powder.

Examples of suitable lubricants are stearic acid and palmitic acid; alkaline and alkaline-earth salts of these acids, such as magnesium and potassium stearate; carbon black, talc, mono- and triglycerides such as glycerol monostearate and glycerol mono-oleate, paraffin oil, and perfluoropolyethers.

The liquid lubricants can be used as solutions or as disperse systems in dispersants.

The amount of liquid lubricant is generally between 0.025 and 25 mg per granule.

The solid lubricants can be applied by dusting the forming chamber and the plungers, that is to say, by covering them with a thin layer of lubricant powder conveyed continuously by a stream of air or other gas so as to achieve optimum dispersion of the solid.

The molding chamber and the plungers can be made of, or coated with, self-lubricating materials, such as polytetrafluoroethylene or ceramic material. This allows to avoid or reduce the use of lubricant.

The catalysts according to the invention preferably have a hollow cylindrical shape with one or more through holes. In the case of catalysts with two or more through holes, the axes are substantially parallel to each other and to the axis of the granule and are substantially mutually lo equidistant.

Preferably, the through holes have a circular cross-section. In the case of catalysts with three through holes, the axes form, relative to the transverse cross-section of the particle, the corners of a substantially equilateral triangle; said corners are orientated towards the points where the transverse cross-section makes contact with the circumscribed circumference. The lobes are preferably cylindrical and circular, identical to each other, and coaxial to the through holes.

The granules may also have a substantially triangular transverse cross-section with rounded corners.

The ratio between the pitch of the holes (i.e., the distance between their respective axes) and the diameter of said holes is preferably between 1.15 and 1.5 and more preferably between 1.3 and 1.4.

The ratio between the height of the particle and the pitch of the holes is preferably between 1.5 and 2.5 and more preferably between 1.7 and 2.3.

In the case of catalysts having a circular transverse cross-section, the ratio between the radius of curvature of each lobe and the pitch of the holes is preferably between 0.6 and 0.9, more preferably between 0.7 and 0.8. The ratio between the radius of curvature of the lobes and the radius of the through holes is preferably between 1.3 and 2.7, more preferably between 1.8 and 2.10. The ratio between the radius of the circle circumscribed about the transverse cross-section and the radius of curvature of the circular lobes is preferably between 1.6 and 2, more preferably between 1.7 and 1.85. The surface-to-volume ratio of each granule in the multilobed version is preferably higher than 2.0 and more preferably higher than 2.2.

In the case of catalysts having a triangular transverse cross-section, the ratio between the radius of curvature of each rounded corner and the pitch of the holes is preferably between 0.6 and 0.9 and more preferably between 0.7 and 0.8. The ratio between the radius of the circle circumscribed to the transverse cross-section and the radius of curvature of each rounded corner is preferably between 1.6 and 2, more preferably between 1.7 and 1.85. The surface-to-volume ratio of each granule, in the version having a triangular cross-section, is preferably higher than 2.0, more preferably higher than 2.2.

In preparing the catalysts according to the invention, the powder containing the precursors and/or active components of the catalyst is dry-mixed or blended with the addition of a small amount of water to obtain a mixture that contains uniformly distributed components.

The resulting mixture is subjected to a drying and/or calcining cycle at temperatures between 120 and 1000° C. for a time that is sufficient to remove the water and the volatile decomposition products.

The pressure used is generally higher than 100 kg/cm² nd can reach 1000 kg/cm² or more.

It has furthermore been found, and this constitutes a further aspect of the present invention, that catalysts with mechanical characteristics, particularly axial ultimate tensile strength, which fall within those of the catalysts that can be obtained by molding with external lubrication can also be achieved by shaping using bulk lubrication, provided that the powder, prior to shaping, is subjected to heat treatments capable of ensuring that the decomposition reactions which occur with weight loss take place before the molding step. In this case, the internal lubricant is used in an amount that is less than 5% by weight.

The resulting powder is suitable for preparing granules of the desired shape and size, using the method of compression-molding.

After molding, the granules are calcined at 600–900° C.

The promoters and stabilizers, such as calcium, magnesium, chromium, molybdenum, and tungsten oxide, can be distributed within the mass of the granule or on its surface. Various methods can be used to provide the surface deposition of the desired components. For example, the component or components can be sprayed onto the granules during tableting after the external lubrication step.

It is furthermore possible to use a lubricant which acts as precursor of the desired compound, for example stearates of alkaline and alkaline-earth metals.

These compounds, after calcination, are converted into the corresponding oxides or mixed oxides or salts.

It is possible to use other mixtures of lubricants and oxides or other catalytically active compounds and spray a thin layer onto the surface of the granules during molding.

As an alternative, it is possible to coat the catalyst granules with a thin layer by working in a stage that is separate from tableting and occurs after it. According to a preferred method, the catalyst granules at the output of the calcination stage are struck, while heated to the temperature of 80–200° C., by a solution or dispersion of the promoter and stabilizing oxides or salts of metals by means of a nebulizer. The concentration of the dispersion, the contact time, and the temperature at which deposition is performed can be changed so as to ensure quick and complete evaporation of the water or other dispersant fluid, in order to form a surface layer having a desired thickness, generally between 0.1 and 100 microns.

In terms of final composition by weight, expressed as oxides, the catalysts comprise 50–92% ferric oxide, 5–20% alkaline metal oxide, 0.5–14% alkaline-earth metal oxide, 2–10% oxide of elements of the lanthanide series, 0.5–6% oxide of a metal of the sixth group of the periodic table.

Potassium oxide is preferred among oxides of alkaline metals, whilst magnesium and calcium oxides are preferred among alkaline-earth ones. Cerium oxide is preferred among lanthanide-series oxides, and molybdenum and tungsten oxides are preferred among group VI oxides.

It is possible to use for example ferric hydroxide, ferric nitrate or carbonate, potassium hydroxide or carbonate, cerium carbonate, or ammonium molybdate as precursors of the active components.

A representative but non-limitative composition is as follows, expressed as oxides by weight percentages:

$Fe_2O_3$=78%; $K_2O$=12%; $CeO_2$=5%; Mg=2%; $WO_3$=0.9%; $MoO_3$=2.1%

Another representative composition, again expressed as a percentage of oxides by weight, is:

$Fe_2O_3$=74%; $K_2O$=6%; $CeO_2$=10%; MgO=4%; $WO_3$=6%

The catalysts having a non-uniform composition, obtained by surface deposition of promoter and stabilizing components on the granules, contain 40–95% iron oxide, 5–30% alkaline metal oxide, 0.05–4% alkaline-earth metal oxide, 0.1–10% oxide of an element of the lanthanide series, 0.05–4% chromium, molybdenum, or tungsten oxide.

In particular, potassium oxide, calcium oxide, magnesium oxide, cerium oxide, and chromium, molybdenum, and tungsten oxides are preferred next to iron oxide.

Examples of preferred but non-limitative compositions are listed hereafter. The asterisk indicates the component that can be deposited on the surface.

| % $Fe_2O_3$ | % $K_2O$ | % $CeO_2$ | % MgO | % CaO | % $Cr_2O_3$ | % $MoO_3$ | % $WO_3$ |
|---|---|---|---|---|---|---|---|
| 78 | 12 | 5 | 2 | 0.09* | / | 2.1 | 0.9 |
| 78 | 14 | 5 | 0.1* | / | / | 2 | 0.9 |
| 74.5 | 16.1 | 9.6 | 4.0 | / | / | / | 5.8 |
| 78 | 12 | 5 | 2.9 | / | / | 2 | 0.1* |
| 78 | 12 | 5 | 4 | / | / | 0.1* | 0.9 |
| 78 | 14 | 5 | 2.8 | / | / | 0.1* | 0.1* |
| 78 | 12 0.1* | 5 | 4.6 | / | 0.1* | 0.1* | 0.1* |

The reaction for the dehydrogenation of ethylbenzene to styrene is usually performed at 540 to 650° C. at pressures which are higher, lower, or equal to the atmospheric pressure. Low pressures are preferred due to thermodynamic reasons, since they allow higher conversions for an equal temperature.

The following examples are provided to illustrate and not to limit the invention.

Analytical determinations

The axial ultimate tensile strength was determined according to ASTM D 4179/82; apparent density (tapped) was determined according to ASTM D 4164/82.

COMPARISON EXAMPLE 1

A paste was prepared by mixing hydrated ferric oxide, cerium carbonate, magnesium carbonate, and tungsten oxide with an aqueous solution of potassium hydroxide, so as to obtain a final catalytic product having the following composition (expressed in % of oxides by weight).

| Oxides | % |
|---|---|
| $Fe_2O_3$ | 76.1 |
| $K_2O$ | 14.0 |
| $CeO_2$ | 6.5 |
| MgO | 2.5 |
| $WO_3$ | 0.9 |

The paste was extruded to form granules with a length of 5 mm and a diameter of 3.5 mm. The extruded granules were dried at 150° C. for 16 hours and then calcined at 400° C. for 2 hours. Some of the granules were calcined at 700° C. for 2 hours. These granules constitute the catalyst 1.

EXAMPLE 1

A second part of the granules prepared according to comparison Example 1 was ground and the powder was tableted, using stearic acid as external lubricant. The plunger and the cylindrical chamber of the tableter were coated with a thin layer of stearic acid, carried continuously by an air stream. Cylinders 4 mm long, with a through hole having a diameter of 2 mm, were tableted. The pressure used was 500 kg/cm². The cylindrical granules were calcined at 700° C. for 2 hours.

This is catalyst no. 2. The axial ultimate tensile strength of this catalyst was 13.4 N/particle.

EXAMPLE 2

A second part of the granules prepared according to comparison Example 1 was ground and tableted (with external lubrication using stearic acid) in a three-lobed shape with three parallel through holes having an inside diameter of 1.3 mm, with a wall thickness of 0.8 mm, a circumference radius of 2.5 mm, and a height of 5 mm. The holes were located at the corners of an equilateral triangle. The tablets were calcined at 700° C. for 2 hours.

This is catalyst no. 3. The axial ultimate tensile strength of this catalyst was 20.9 N/particle.

EXAMPLE 3

A catalyst having the following composition by weight, expressed as oxides, was prepared with the method of comparison Example 1:

$Fe_2O_3$=74.5%; $K_2O$=6.1%; $CeO_2$=9.6%; MgO=4.0%; $WO_3$=5.8%

$Fe_2O_3$ in the red spheroidal form was used as $Fe_2O_3$. $K_2O$ as introduced as KOH.

Calcination was performed at 800° C. for 4 hours.

This is catalyst no. 4.

EXAMPLE 4

Part of the granules prepared according to Example 3 was ground and tableted according to the method of Example 2 so as to obtain three-lobed granules with three holes, having the characteristics specified in Example 2.

Mg stearate was used instead of stearic acid as external lubricant.

The axial ultimate tensile strength of this catalyst was 32 N/particle; 38% of the volume was formed by pores having a radius of 600 to 800 Å, 11% by pores having a radius of 800 to 1000 Å, 12% by pores having a radius of 1000 to 2000 Å, and 6% by pores having a radius of 2000 to 4000 Å.

There were no macroporosities with a radius of more than 50000 Å.

The surface area of the catalyst was 4.9 $m^2/g$; porosity was 0.17 ml/g.

This is catalyst no. 5.

EXAMPLE 5

Catalysts no. 1, 2, 3, 4, and 5 were tested in a steel reactor with an inside diameter of 35 mm. In each test, 200 $cm^3$ of catalyst were placed in the reactor and supported with a steel grille. Tests at 570°, 590°, and 610° C. were conducted for each catalyst; in these tests, water vapor and ethylbenzene, preheated to the above temperatures, were passed through the catalytic bed with a water/ethylbenzene ratio of 2.4 by weight; the output pressure was 1.05 atm and the hourly spatial velocity of the ethylbenzene was 0.5. Samples of the reaction products were collected over 2 hours after the system had been stabilized for at least 20 hours for each condition. The percentages of conversion and molar selectivity are listed in the following table.

TABLE 1

| | Temperature(° C.) | Conversion % | Selectivity % |
|---|---|---|---|
| Cat. 1 | 570 | 50.31 | 93.3 |
| BD = 1.08 | 590 | 62.47 | 91.34 |
| | 610 | 74.62 | 88.05 |
| Cat. 2 | 570 | 54.66 | 93.34 |
| BD = 1.01 | 590 | 64.85 | 91.52 |
| | 610 | 75.34 | 88.73 |
| Cat. 3 | 570 | 55.12 | 93.53 |
| BD = 0.857 | 590 | 65.43 | 91.70 |
| | 610 | 76.17 | 89.08 |

TABLE 1-continued

| | Temperature(° C.) | Conversion % | Selectivity % |
|---|---|---|---|
| Cat. 4 | 570 | 60 | 88 |
| BD = 1.42 | | | |
| Cat. 5 | 570 | 60 | 90.5 |
| BD = 1.08 | | | |

BD = apparent density in g/ml.

What is claimed is:

1. Catalysts in the form of granules having a cylindrical shape, provided with one or more through holes which are parallel to each other and to the axis of the granule, when more than one hole is present, having a porosity between 0.15 and 0.35 $cm^3/g$ and wherein, in the pore radius distribution curve, over 50% of the pores have a radius of more than 600 Å and wherein there are no macroporosities with a radius of more than 50,000 Å, usable in the dehydrogenation of ethylbenzene to styrene, comprising, as active components, ferric oxide and promoters chosen among oxides of alkaline and alkaline-earth metals, oxides of the lanthanide series, and chromium, tungsten, and molybdenum oxides, obtained by compression molding of powders of the promoters and of the active components, and of precursors thereof, by using, for lubrication, as sole lubricant, a lubricant applied to the walls of the molding chamber and to the plungers of the mold.

2. Catalysts according to claim 1 in the form of multilobed granules with lobes which are coaxial to the through holes.

3. Catalysts according to claim 2, provided with three holes, wherein the ratio between the pitch of the holes and the diameter of said holes is between 1.15 and 1.5 and the ratio between the height of the granules and the pitch of the holes is between 1.5 and 2.5.

4. Catalysts according to claim 2 in the form of multilobed granules with lobes which are coaxial to the axis of the holes and wherein the ratio between the pitch of the holes and the diameter thereof is between 1.15 and 1.5 and the ratio between the height of the granules and the pitch of the holes is between 1.5 and 2.5.

5. Catalysts according to claim 1 in the form of multilobed granules with lobes which are coaxial to the axis of the holes and wherein the ratio between the pitch of the holes and the diameter thereof is between 1.15 and 1.5 and the ratio between the height of the granules and the pitch of the holes is between 1.5 and 2.5.

6. Catalysts in the form of granules having a geometric shape, provided with one or more through holes, usable in the dehydrogenation of ethylbenzene to styrene, and comprising, as active components, ferric oxide and promoters chosen among oxides of alkaline and alkaline-earth metals, oxides of the lanthanide series, and chromium, tungsten, and molybdenum oxides, having an axial ultimate tensile strength (in the direction of the axis of the holes) of more than 15 N/particle, said catalysts being obtained by compression-molding of powders of the precursor and of the active components, and of precursors thereof by using, for lubrication, as sole lubricant, a lubricant applied to the walls of the molding chamber and to the plungers of the mold.

7. Catalysts according to claim 6, wherein the ultimate tensile strength is between 20 and 80 N/particle.

8. Catalysts in the form of granules having a cylindrical shape, provided with one or more through holes which are parallel to each other and to the axis of the granule, when more than one hole is present, usable in the dehydrogenation of ethylbenzene to styrene, and comprising, as active components, ferric oxide and promoters chosen among oxides of alkaline and alkaline-earth metals, oxides of the lanthanide series, and chromium, tungsten, and molybdenum oxides, obtained by compression molding of powders of the active components and the promoters, and of precursors thereof by using, for lubrication as sole lubricant, a lubricant applied to the walls of the molding chamber and to the plungers of the mold.

9. Catalyst in the form of granules having a cylindrical shape, provided with one or more through holes, which are parallel to each other and to the axis of the granule, when more than one hole is present, usable in the dehydrogenation of ethylbenzene to styrene, comprising, ferric oxide as active component and promoters chosen among oxides of alkaline and alkaline-earth metals, oxides of the lanthanide series, and chromium, tungsten and molybdenum oxides, obtained by compression molding of powders of the active components and promoters and of precursors thereof, wherein for lubrication a lubricant is used dispersed in the bulk of the powder to be compression molded, and the powder containing the lubricant is heat-treated prior to the compression molding step to remove the volatile compounds which form during the calcination step.

10. Catalysts in the form of granules having a cylindrical shape, provided with one or more through holes which are parallel to each other and to the axis of the granule, when more than one hole is present, usable in the dehydrogenation of ethylbenzene to styrene, and comprising, as active components, ferric oxide and promoters chosen among oxides of alkaline and alkaline-earth metals, oxides of the lanthanide series and chromium, tungsten, and molybdenum oxides, obtained by compression molding of powders of the active components and of the precursors thereof, and optionally of promoters, by using, for lubrication as sole lubricant, a lubricant applied to the walls of the molding chamber and to the plungers of the mold, and wherein one or more of the promoters and precursors thereof are comprised in a surface layer having a thickness from 0.1 to 100 microns.

11. Process for the dehydrogenation of ethylbenzene to styrene, wherein catalysts chosen among those according to claim 1 are used.

12. Process according to claim 11, wherein the weight ratio of steam/ethylbenzene used in the dehydrogenation of ethylbenzene is higher than 1.5.

* * * * *

UNITED STATES PATENT AND TRADEMARK OFFICE
CERTIFICATE OF CORRECTION

PATENT NO. : 6,166,280
DATED : December 26, 2000
INVENTOR(S) : Carlo Rubini, et al.

It is certified that error appears in the above-identified patent and that said Letters Patent is hereby corrected as shown below:

Title page,
Item [75] Inventors, please change "Rubin" to -- Rubini --;
Item [54], please change "CATALYST" TO -- CATALYSTS --;
Item [73] Assignee, please change "Technologies" to -- Technologies --;

Signed and Sealed this

Sixteenth Day of October, 2001

Attest:

NICHOLAS P. GODICI
Attesting Officer  Acting Director of the United States Patent and Trademark Office

UNITED STATES PATENT AND TRADEMARK OFFICE
CERTIFICATE OF CORRECTION

PATENT NO.    : 6,166,280
DATED         : December 26, 2000
INVENTOR(S)   : Carlo Rubini et al.

It is certified that error appears in the above-identified patent and that said Letters Patent is hereby corrected as shown below:

<u>Title page,</u>
Item [54], please change "CATALYST" to -- CATALYSTS --;
Item [75], Inventors, please change "Rubin" to -- Rubini --;
Item [73], Assignee, please change "Technologies" to -- Tecnologic --;

This certificate supersedes Certificate of Correction issued October 16, 2001.

Signed and Sealed this

Twenty-sixth Day of November, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO.   : 6,166,280
DATED        : December 26, 2000
INVENTOR(S)  : Carlo Rubini et al.

Page 1 of 1

It is certified that error appears in the above-identified patent and that said Letters Patent is hereby corrected as shown below:

<u>Title page,</u>
Item [54], please change "CATALYST" to -- CATALYSTS --;
Item [75], Inventors, please change "Rubin" to -- Rubini --;
Item [73], Assignee, please change "Technologies" to -- Tecnologie --

This certificate supersedes Certificate of Correction issued November 26, 2002.

Signed and Sealed this

Sixth Day of May, 2003

JAMES E. ROGAN
*Director of the United States Patent and Trademark Office*